US006600047B2

(12) United States Patent
Benneker et al.

(10) Patent No.: US 6,600,047 B2
(45) Date of Patent: Jul. 29, 2003

(54) PROCESS FOR MAKING AMLODIPINE MALEATE

(75) Inventors: Franciscus B. G. Benneker, Rheden (NL); Pavel Slanina, Lelekovice (CZ); Frantisek Picha, Brno (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 09/938,841

(22) Filed: Aug. 27, 2001

(65) Prior Publication Data

US 2002/0086888 A1 Jul. 4, 2002

Related U.S. Application Data

(63) Continuation-in-part of application No. 09/809,343, filed on Mar. 16, 2001, now abandoned.
(60) Provisional application No. 60/258,612, filed on Dec. 29, 2001.

(51) Int. Cl.⁷ ............................................. C07D 211/86
(52) U.S. Cl. ...................................... 546/321; 514/356
(58) Field of Search ........................... 546/321; 514/356

(56) References Cited

U.S. PATENT DOCUMENTS

| | | | | |
|---|---|---|---|---|
| 4,294,969 A | * | 10/1981 | Baldwin et al. | 546/318 |
| 4,430,333 A | * | 2/1984 | Campbell et al. | 546/257 |
| 4,572,909 A | * | 2/1986 | Campbell et al. | 514/356 |
| 4,845,113 A | * | 7/1989 | Gandolfi et al. | 514/356 |
| 4,870,091 A | * | 9/1989 | Peglion et al. | 514/356 |
| 4,879,303 A | | 11/1989 | Davison et al. | |
| 4,983,740 A | | 1/1991 | Peglion et al. | |
| 5,068,337 A | * | 11/1991 | Archibald et al. | 514/256 |
| 5,155,120 A | | 10/1992 | Lazar et al. | |
| 5,389,654 A | | 2/1995 | Furlan et al. | |
| 5,438,145 A | | 8/1995 | Furlan et al. | |
| 6,046,337 A | | 4/2000 | Bozsing et al. | |

FOREIGN PATENT DOCUMENTS

| | | |
|---|---|---|
| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

Alker et al., "Long–acting dihydropyridine calcium antagonists. 9. Structure activity relationships around amlodipine", Eur J Med Chem (1991) 26, 907–913.
Amlodipine Besylate Monograph, PHARMEUROPA vol. 10, No. 2, 197–198, Jun. 1998.
Faulkner et al, "Absorption of Amlodipine Unaffected by Food", Arzneim Forsch/Drug Res. 39 (11), No. 7, (1989).
McDaid and Deasy, "Formulation development of a transdermal drug delivery system for amlodipine base", International Journal of Pharmaceutics 133 (1996) 71–83.
Arrowsmith et al., "Long–Acting Dihydropyridine Calcium Antagonists. 1. 2–Alkoxymethyl Derivatives Incorporating Basic Substituents", J. Med. Chem. American Chemical Society, 1986, 29, 1696–1702.
FDA FOIA Material on Amlodipine Besylate, NDA No. 19–787, "Review of an Original NDA", Oct. 10, 1990.

* cited by examiner

*Primary Examiner*—Jane Fan
(74) *Attorney, Agent, or Firm*—Fleshner & Kim, LLP (57) ABSTRACT

A process for making amlodipine maleate comprises reacting amlodipine or an acid addition salt thereof with maleic acid under an acidic environment to form an amlodipine maleate product. The process allows for the formation of amlodipine maleate substantially free from amlodipine aspartate.

24 Claims, 3 Drawing Sheets

PROCESS FOR MAKING AMLODIPINE MALEATE

This application is a continuing application under 35 U.S.C. §120 of prior U.S. patent application Ser. No. 09/809,343, filed Mar. 16, 2001 now abandoned, the entire contents of which are incorporated herein by reference. Further, this application claims the benefit of priority under 35 U.S.C. §119(e) from U.S. provisional application No. 60/258,612, filed Dec. 29, 2001, the entire contents of which are incorporated herein by reference.

BACKGROUND OF THE INVENTION

1. Field of the Invention

The present invention relates to a process for making amlodipine maleate with good purity.

2. Description of the Related Arts

Calcium channel blockers (calcium antagonists) are useful in treating cardiac conditions including angina and/or hypertension. Dicarboxylate-dihydropyridine derivatives are generally known to possess calcium channel blocking activity. For example, EP 089 167 and corresponding U.S. Pat. No. 4,572,909 disclose a class of 2-amino group-3,5-dicarboxylate dihydropyridine derivatives as being useful calcium channel blockers. These patents identify that one of the most preferred compounds is 2-[(2-aminoethoxy)methyl]-4-(2-chlorophenyl)-3-ethoxycarbonyl-5-methoxycarbonyl-6-Methyl-1,4-dihydropyridine. This compound, which is now commonly known as amlodipine, has the following formula:

Amlodipine exhibits good bioavailability and has a long half-life in the body. While a variety of acid addition salts are taught in these patents to be suitable, the maleate salt is identified as the most preferred acid addition salt. Examples 9, 11, 12 and 22 of EP 89167 as well as J. Med. Chem. 29, 1698 (1986) disclose the preparation of amlodipine maleate (with 1:1 molar ratio of both components) by dissolving a reaction mixture containing an in situ prepared raw amlodipine base into ethyl acetate or into ethanol and adding thereto solid maleic acid whereby the maleate salt of amlodipine precipitates. The salt is then isolated by filtration and recrystallized from ethyl acetate or from acetone/ethyl acetate 1:1 mixture.

However, the commercial product of amlodipine (NORVASC by Pfizer) uses amlodipine besylate (benzene sulfonate) and not amlodipine maleate. Indeed, subsequent patents EP 244 944 and corresponding U.S. Pat. No. 4,879,303 indicate that the besylate salt provides certain advantages over the known salts including good formulating properties. Apparently, amlodipine maleate suffered from tabletting and stability problems so as to cause a switch during development to the besylate salt. (See "Review of Original NDA" for NDA# 19-787 of 10.10.1990, obtainable from FDA under Freedom of Information Act). The stability and tabletting issues/causes are not publicly disclosed in the information available from the FDA.

SUMMARY OF THE INVENTION

The present invention relates to the discovery of a heretofore undisclosed impurity associated with amlodipine maleate and to a process for preventing its formation during production. Specifically, the present invention relates to a process that comprises reacting amlodipine or a pharmaceutically acceptable salt thereof with maleic acid under an acidic environment to form an amlodipine maleate product. Typically the process relates to the manufacture of an amlodipine maleate salt substantially free of amlodipine aspartate, which comprises the steps of (a) either (1) adding, continuously or portionwise, a source of amlodipine into a solution or suspension of maleic acid to form a solution, wherein the relative molar amount of maleic acid to amlodipine being added is at least 1.01:1 or (2) contacting, continuously or portionwise, a source of amlodipine with a solution or suspension of maleic acid under pH control to form a solution whereby the pH of the solution does not exceed 6.5; and (b) separating amlodipine maleate in a solid form from the solution. Further the present invention relates to a process of purification of amlodipine maleate, which comprises crystallizing or precipitating amlodipine maleate from a solution thereof wherein said solution comprises an excess of maleic acid.

DETAILED DESCRIPTION OF THE INVENTION

Figure 1:
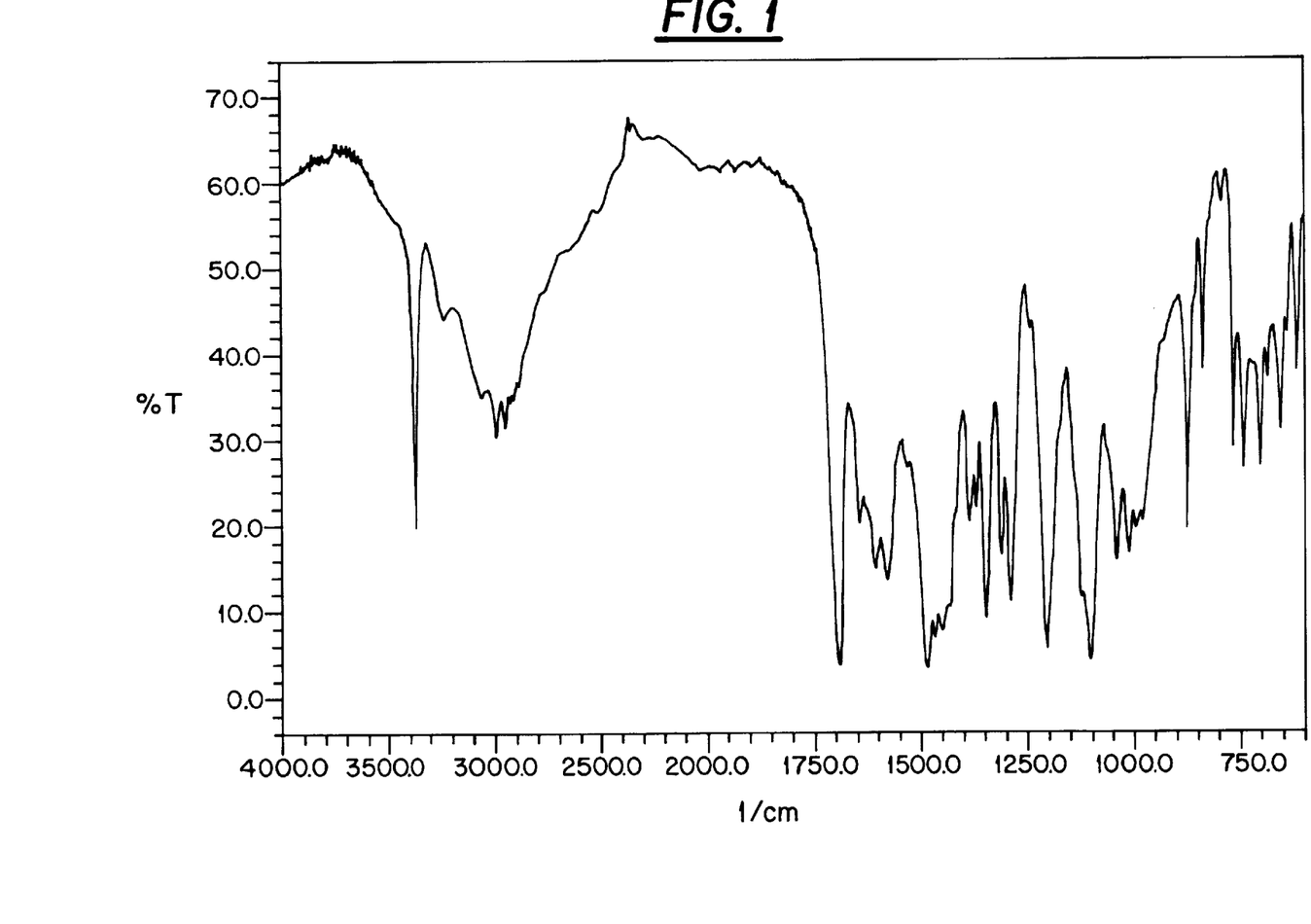
FIG. 1 shows the IR plot for the material of Example 1.
Figure 2:
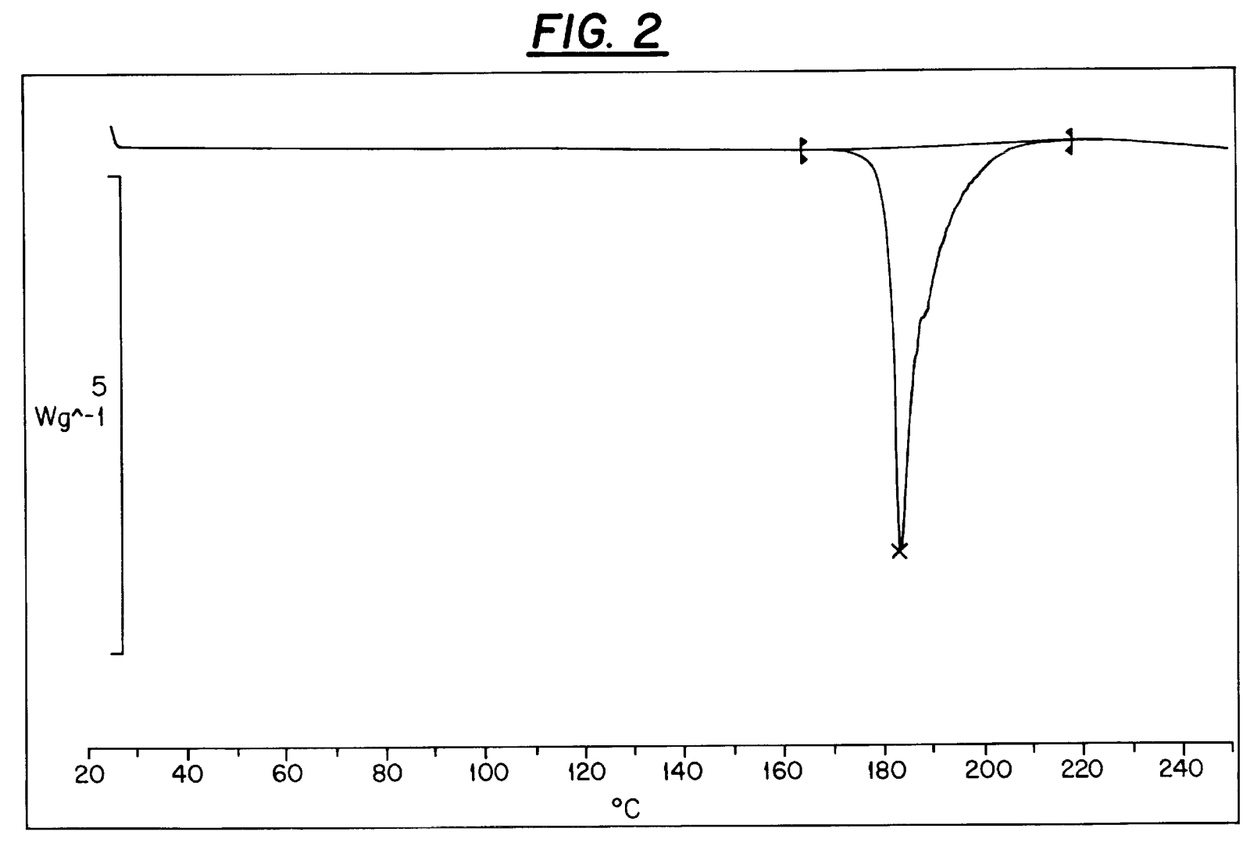
FIG. 2 shows the DSC curve for the material of Example 1.
Figure 3:
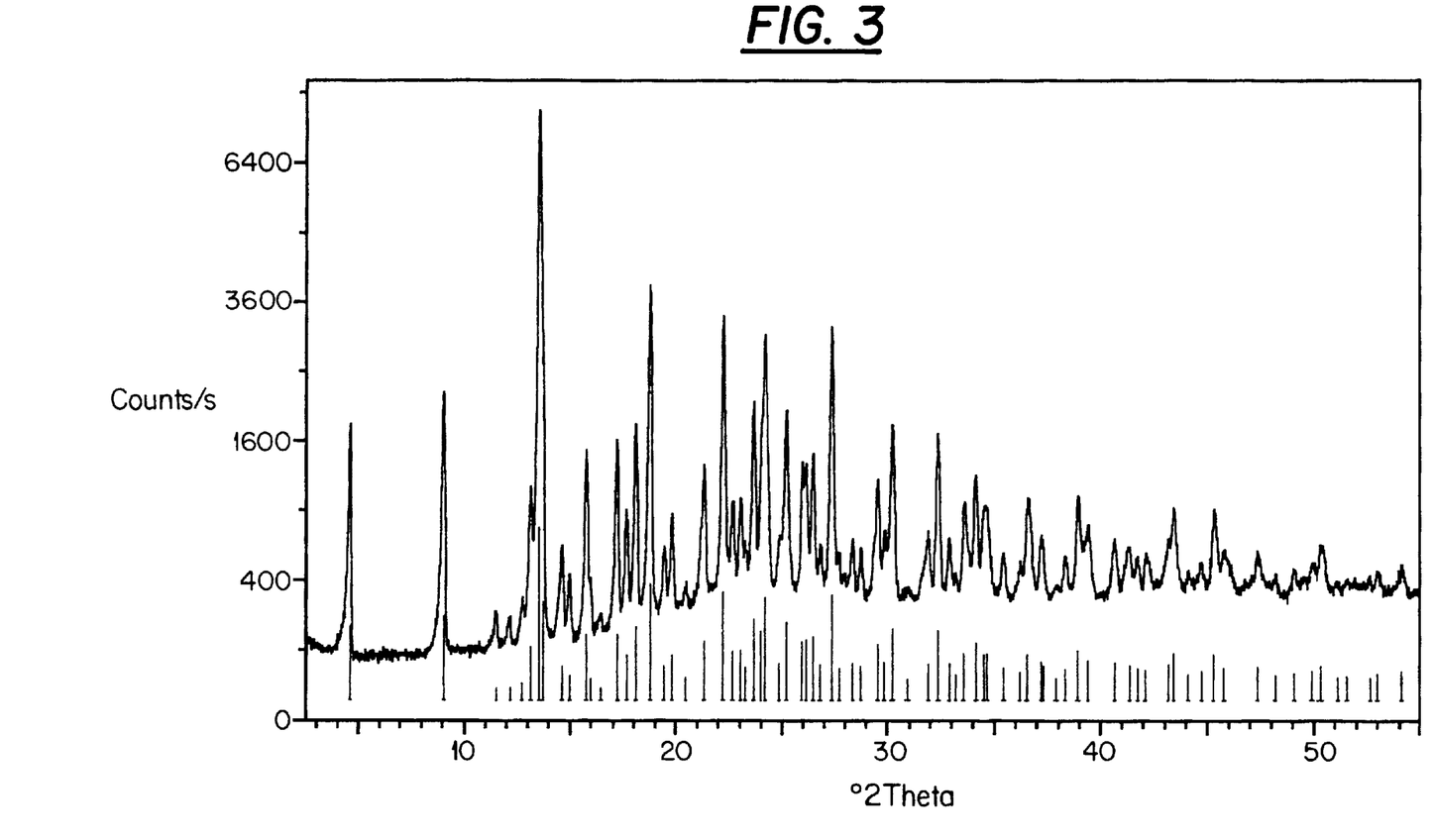
FIG. 3 shows the x-ray diffractogram for the material of Example 1.

Though the process of converting amlodipine free base or salt into an amlodipine maleate salt is essentially simple, it has now been discovered that the known procedures for manufacturing amlodipine maleate may give rise to substantial amounts of a side product represented by the formula (1):

The compound of formula (1), which is hereinafter referred to as "amlodipine aspartate," is a side product associated only with maleate salts of amlodipine as it is formed by a Michael addition reaction of the amino group of amlodipine to the double bond of the maleic acid.

It has now been discovered that the production procedure described in the above-cited patents and literature may produce negligible amounts of amlodipine aspartate as a by-product in a laboratory scale, but that substantial increases in amlodipine aspartate by-product are likely on a production scale, namely at enhanced temperatures which are needed for complete conversion and for obtaining amlodipine maleate in a good crystalline form.

The presence of a side product in any substance intended to be administered to a human patient as a therapeutic agent is generally undesirable. Removing side products and impurities can result in higher production costs and lower yields due to the loss of material in the purification step. It is thus advantageous to form the desired product in the first instance with as few side products and impurities as possible.

The present invention is based on the finding that amlodipine maleate may be prepared substantially free from amlodipine aspartate by careful selection of reaction conditions. Namely, it was found that the pH of the reaction mixture during the formation of amlodipine maleate should be essentially acidic. A process for manufacture of an amlodipine maleate salt substantially free of amlodipine aspartate comprising a reaction of amlodipine with maleic acid, whereby the reaction environment is essentially acidic, thus forms a basic aspect of the invention.

Accordingly, a first embodiment of the present invention comprises adding the starting material containing amlodipine (herein under: "source of amlodipine") to a solution of maleic acid in such a way that maleic acid is in excess to amlodipine in the reaction mixture; i.e., by adding amlodipine base to a molar equivalent or excessive amount maleic acid and preferably to an excess thereof. The unreacted maleic acid present during the addition of the amlodipine source provides an acidic pH for the reaction mixture during salt formation. Preferably, a free base of amlodipine or another acid addition salt of amlodipine is added into a solution or suspension of maleic acid in a suitable solvent to form a solution wherein the amount of maleic acid is at least 1.01 times the molar amount of amlodipine, preferably at least 1.05 times the molar amount of amlodipine. After addition, amlodipine maleate separates out in a solid state. In this process, the amlodipine reagent is employed in a solid state or in a solution or in a suspension and may be charged continuously or portionwise. A suitable minimum excess of maleic acid is about 1 molar percent or more, i.e. of about 1.01 molar equivalents, an advantageous extent is of about 5 molar percent, and may be even substantially higher, e.g. up to 50 or 100 molar percent, i.e. 2 molar equivalents. The use of an excess amount of maleic acid is advantageous for industrial scale production, where the actual amount of the charged amlodipine may be in some cases be difficult to determine.

A second embodiment of the invention comprises contacting an amlodipine source with maleic acid in a solvent under pH control, whereby the pH value is maintained below the value of 7, preferably below 6.5, and typically in the range between 4.5 to 6.5, optionally by portionwise or continuous addition of maleic acid. At pH lower than 4.5, the formation of amlodipine aspartate is sufficiently suppressed as well but other side products may sometimes be formed. Generally it is most convenient, even under pH control, to add the amlodipine source to the maleic acid as in the first embodiment, but this is strictly speaking not required. After addition, amlodipine maleate separates out in a solid state.

This process of monitoring the pH is also useful in the case where the source of amlodipine is an unpurified material, as the actual content of amlodipine therein is normally only approximated and/or the amlodipine source may also contain impurities or side products of a basic nature, which may also react with maleic acid. For instance, a raw amlodipine obtained from deprotection of phthalimido-amlodipine by an excess of methylamine may contain traces of methylamine, the amount of which is determinable only with difficulties. Thus, the pH of the reaction mixture is monitored during the addition or treatment of the maleic acid solution, or suspension, with the source of amlodipine and adjusted such as by addition of acid, preferably maleic acid, as needed to maintain pH control under the value of less than 7 as described above.

Alternatively, the pH can be maintained in the acidic region by using an acid addition salt of amlodipine other than the maleate. The necessary acidic pH is adjusted by liberation of the corresponding acid from such salt during the formation of the maleate, as illustrated by the equation:

Wherein X is an anion of the corresponding acid.

As this reaction proceeds essentially in an equilibrium state, amlodipine salts should be employed which are more soluble in the reaction medium than amlodipine maleate. As the amlodipine maleate separates out from the solution, the equilibrium is continuously shifted towards the formation of the next amlodipine maleate. Suitable salts are e.g. amlodipine hydrochloride, methane sulfonate or benzenesulfonate. In general, any suitable salt which is more soluble in the reaction solvent then amlodipine maleate may be used.

In processes of the invention, various sources of amlodipine may be used for reaction with maleic acid. For instance, there may be used a reaction mixture obtained after the final step of amlodipine synthesis. Such processes are known from prior art and the final steps thereof usually comprise deprotection of an amino-protecting group in an amlodipine precursor as outlined in the following scheme:

In the scheme, N-Prot represents a substituent or group protecting or masking the amino-group; it may comprise a benzylamino or phthalimido group (EP 89 167), azido group (EP 89 167), tritylaminogroup (EP 599220), hexamethylenetetramino group (EP 902016) etc. Another useful synthesis scheme for making amlodipine or salts thereof in good yields and purity via a phthalimidoamlodipine intermediate is described in commonly-owned provisional application Ser. No. 60/258,613, filed Dec. 29, 2000, the entire contents of which are incorporated herein by reference, and in commonly-owned co-pending U.S. patent application Ser. No. 09/809,351, filed on Mar. 16, 2001, and entitled "Process for Making Amlodipine, Derivatives Thereof, and Precursors Therefor," the entire contents of which are incorporated herein by reference.

After the deprotection reaction, the reaction mixture may be treated by known methods to provide advantageously a solution of raw amlodipine in a suitable solvent. Such a solution may be used as the amlodipine source for the formation of the amlodipine maleate essentially free from amlodipine aspartate by the process of the present invention. As an alternative, amlodipine free base obtained by the amlodipine synthesis may be isolated in a solid state, e.g. by a process outlined in Int. J. Pharm. 133, 72 (1996) and the free base may be charged in a crude or purified state. In another alternative, amlodipine free base (with or without isolation thereof) may also be converted to a salt other than the maleate prior to the contact with maleic acid. The amlodipine source can be in dissolved form in a solvent, a solid state material or a suspension.

As pointed above, the common key aspect of any of the process of our invention is that the source of amlodipine is contacted with maleic acid in an acidic environment. In general, the pH of reaction mixture should not exceed the value of approximately 6.5 during the salt formation reaction.

Various solvents or solvent systems may be applicable in the process of our invention. The preferred solvents are those in which the starting materials are sufficiently soluble and in which the produced amlodipine maleate is only sparingly soluble. Such solvents comprise water, an alcohol such as methanol, ethanol or isopropanol, an ester such as ethyl acetate, a ketone such as acetone, a nitrile such as acetonitrile, an ether such as dioxan or tetrahydrofuran, a carbohydrate such as toluene or mixtures thereof. It is an advantage of the present invention that certain solvents which are inconvenient to be used in the prior art procedures, such as water, may be used without difficulty in the present process.

The temperature during the contacting of the amlodipine source with maleic acid may vary from ambient temperature to the boiling point of the solvent or solvent system and may vary also during the course of reaction. Preferred are temperatures are higher than 40° C. as amlodipine maleate crystallizes from a hot solution as good and/or large crystals. If working at ambient temperature, amlodipine maleate precipitates in small crystals that are frequently difficult to filter and dry. However, the formation of amlodipine aspartate is temperature dependent. It has been observed that when maleic acid is added to amlodipine base as in the process of prior art, undesirable amounts of the amlodipine aspartate are formed at temperatures higher than about 40° C. For instance, the addition of maleic acid to amlodipine base in isopropanol at 80° C. may produce amlodipine maleate impurified with approx. 0.7% of the aspartate. However, as in accordance with the preferred aspects of the invention, wherein the amlodipine is added to the maleic acid, higher temperatures can be used without difficulty. This is especially advantageous when the reaction temperature is higher than 40° C., e.g. if a solvent is used which requires higher temperatures to convert amlodipine or maleic acid into a solution or if the reaction mixture should be concentrated by evaporation. For instance, addition of amlodipine base to 5% molar excess of maleic acid in hot isopropanol yielded amlodipine maleate with only 0.03% of aspartate.

The importance of the essentially acidic environment, especially the presence of an excess of maleic acid, in respect to minimization of the rate of formation of amlodipine aspartate may be manifested also in processes of purification of amlodipine maleate from other impurities by crystallization or precipitation. Elevated temperatures which are necessary for dissolving amlodipine maleate in a crystallization or precipitation solvent may contribute to the formation of amlodipine aspartate as well. As the solubility of amlodipine aspartate is similar in most crystallization solvents, common crystallization techniques do not allow to separate amlodipine maleate therefrom and thus, ironically, the crystallization rather "impurifies" the product. If, however, an excess of maleic acid is present in the crystallization system, the formation of amlodipine aspartate is minimised. Thus a further aspect of the present invention relates to a process of separating amlodipine maleate in a solid state from a solution by precipitation or crystallization, characterised in that free maleic acid in amount from 1% to 100% molar excess, preferably in amount of about 5% molar excess, is present during the separation.

The precipitation or crystallization of amlodipine maleate from a solution having an excess of maleic acid can thus be used as a purification step. Another aspect of the present invention comprises forming purified amlodipine free base or salts thereof by conversion of the precipitated or crystallized amlodipine maleate. Specifically, once the amlodipine maleate is precipitated or crystallized from a solution containing an excess of maleic acid, it can be converted to another salt of amlodipine with good purity. Conversion can be carried out directly by treating the amlodipine maleate in solution with a suitable acid. Alternatively, conversion can also include treating the amlodipine maleate in solution with a base, either organic or inorganic base, to form amlodipine free base followed by treatment of the free base, with or without isolation thereof, with the desired acid to form the intended amlodipine salt. The new salt can be precipitated or otherwise removed from the solvent. Because of the purity of the precipitated or crystallized amlodipine maleate, it along with the converted salt forms and optional free base, may be produced in pharmaceutically acceptable quality, essentially without any subsequent purification. Examples of salts preparable by this process include amlodipine benzene sulfonate (besylate), amlodipine methane sulfonate (mesylate) and amlodipine hydrochloride.

In common solvents suitable for crystallization of amlodipine maleate such as water, methanol, ethanol, isopropanol, acetone, acetonitrile, ethyl acetate, toluene and mixtures thereof, the necessary excess of maleic acid should be at least 1 molar percent and up to 100 molar percent, advantageously between 5 to 25 molar percent. Proper extent of maleic acid useful in an industrial process may be determined in each particular case by ordinary set of experiments, taking the solvent, concentration and temperature regimen into consideration and having the yield and purity as the criteria of evaluation.

The amlodipine maleate that is "substantially free" from amlodipine aspartate means that the amlodipine maleate contains less than 1 wt %, preferably less than 0.5 wt %, more preferably less than 0.2 wt %, and most preferably less than 0.1 wt % of amlodipine aspartate. The amlodipine maleate substantially free from amlodipine aspartate may be used in therapy as a pharmaceutically acceptable salt of amlodipine. Accordingly, amlodipine maleate substantially free from amlodipine aspartate forms another aspect of the present invention.

The molecule of amlodipine has a chiral centre on the 1,4-dihydropyridine ring and exists in two optically active forms. The forms may be separated by crystallisation or chromatography, optionally in the form of a salt, for example a salt with an optically active base or acid, and may be accordingly converted into individual isomers of amlodipine maleate of our invention by processes described above. The individual isomers of amlodipine or their mixtures can be used in the present invention. Correspondingly, the individual or mixed isomers of amlodipine maleate substantially free from amlodipine aspartate are also within the scope of this invention.

Amlodipine maleate substantially free from amlodipine aspartate may be used as a calcium channel blocker and thus can be used to treat any cardiac condition that would be benefited by administration of a calcium channel blocker. In particular, the amlodipine maleate free from amlodipine aspartate can be used to treat or prevent hypertension or angina by administering an effective amount to a patient in need thereof. The specific form of angina is not particularly limited and specifically includes chronic stable angina pectoris and vasospastic angina (Prinzmetal's angina). The compound is also useful in reducing heart failure symptoms, improving systolic left ventricular function and increasing exercise capacity in patients with ischaemic LVD and heart failure without current angina. The compound can be administered by any suitable route including orally or parenterally. The "patients" intended to be treated include human and non-human animals especially humans and non-human mammals.

The compound is usually administered as part of a pharmaceutical composition. Accordingly, a further aspect of the invention is a pharmaceutical composition for treating or preventing hypertension or angina that comprises an effective amount of amlodipine maleate substantially free from amlodipine aspartate and a pharmaceutically acceptable excipient. Excipients include any inert or non-active material used in making a pharmaceutical dosage form. For example, tablet excipients include, but are not limited to, calcium phosphate, cellulose, starch or lactose. Capsules such as those made of gelatin, may contain or carry amlodipine maleate alone or in admixture with other excipients. Liquid dosage forms are also included such as oral liquids in the form of liquors or suspensions, as well as injectable solutions. The pharmaceutical composition may be formulated for transdermal administration in the form of a patch. All of the above described pharmaceutical compositions may optionally contain one or more of each of the following excipients: carriers, diluents, colorants, flavoring agents, lubricants, solubilizing agents, disintegrants, binders and preservatives.

The pharmaceutical composition is normally provided in a unit dose. A unit dose is typically administered once or twice daily, more typically once daily. In the case of a transdermal patch, the unit dose (one patch) is generally applied at least once a month, more commonly at least once a bi-week, and typically once a week. An effective amount of amlodipine maleate free from amlodipine aspartate in a unit dose for treating or preventing hypertension or angina is generally within the range of 1 to 100 mg, typically 1 to 50 mg, more typically 1 to 20 mg. In solid oral dosage forms (tablets, capsules, etc.), the pharmaceutical composition typically contains about 1, 2.5, 5.0, or 10 mg of the amlodipine maleate. For simplicity, all amounts refer to the corresponding amount of amlodipine free base provided to the composition. The usual initial human oral dose of amlodipine for both hypertension and angina is 5 mg once daily with a maximum dose of 10 mg once daily. Small, fragile, or elderly individuals, or patient with hepatic insufficiency may be started at 2.5 mg once daily and this dose may be used when adding amlodipine to other antihypertensive therapy. Specific examples of pharmaceutical compositions include those described in EP 244944 wherein amlodipine maleate according to the present invention is used as the active ingredient.

Preferred pharmaceutical compositions will have a pH within the range of from about 5.5 to 7.0, when measured as a 20 wt % aqueous slurry as is described in more detail in commonly-owned co-pending U.S. patent application Ser. No. 09/809,346, filed on Mar. 16, 2001, and entitled "Pharmaceutical Compositions Comprising Amlodipine Maleate," the entire contents of which are incorporated herein by reference. These compositions generally provide good or improved stability.

All of the pharmaceutical compositions described above can be made by known methods and techniques. For example, the tablets can be made by dry granulation/direct compression or by a classical wet granulation method. Typically, tablets are made by blending, filling and compressing into tablets. The blending step may comprise a wet granulation or dry granulation. Similarly, capsules can be made by blending the ingredients and filling the capsule.

Amlodipine maleate substantially free from amlodipine aspartate may also be used in combination with other antihypertensive and/or antianginal agents, for instance with ACE-inhibitors such as benazepril. The combination may be in the form of a single combination preparation, e.g. a capsule containing amlodipine maleate and benazepril hydrochloride, or by separate administration of drugs containing the above agents. Similarly amlodipine maleate substantially free from amlodipine aspartate may also be combined with HMG-CoA reductase inhibitors such as lovastatin, simvastatin, atorvastatin as well as other statins.

In preparing amlodipine maleate as an active ingredient or in a pharmaceutical composition, it may be beneficial to assay for the presence and/or amount of amlodipine aspartate in order to insure that the active or compositional forms are sufficiently free from the aspartate impurity. This is useful in checking, for example, the effectiveness of the crystallization conditions chosen for making amlodipine maleate substantially free from amlodipine aspartate in accordance with the present invention. Assaying for amlodipine aspartate as well as how to make amlodipine aspartate as a reference standard or reference marker composition is described more fully in co-pending commonly owned U.S. patent application Ser. No. 09/809,347, filed on Mar. 16, 2001, and entitled "Reference Standards For Determining The Purity Or Stability Of Amlodipine Maleate And Processes Therefor," the entire contents of which are incorporated herein by reference.

EXAMPLES

Example 1

Amlodipine Maleate from Crude Amlodipine

Step 1 Decomposition of Phthalimidoamlodipine

The reactor A1 is charged with 64 l of 40% aqueous methylamine and 8.0 kg of phthalimidoamlodipine under stirring. The suspension is stirred at 40–45° C. for 8 hours. Then 120 l of toluene is added and the mixture is stirred for 30 minutes. Then the mixture is allowed to stand for separation of layers, the aqueous layer is separated and discarded. The toluene layer is washed with 40 l of water. The toluene solution is concentrated on a rotary evaporator at 60° C. until the first precipitate occurs (the volume approx. 12 liters). The residue is poured into a container and the evaporator is washed with 4 l of ethanol which is combined with the toluene solution. The content of amlodipine in the solution is determined by titration. Result: 6.13 kg.

Step 2 Formation of Amlodipine Maleate 1.83 kg of maleic acid is dissolved in 70 l of ethanol at 50–55° C. in reactor A2. The solution is filtered through pressure filter into the clean reactor A1. The reactor A2 and the filter are washed with 7 l of ethanol. The temperature of the combined solution is adjusted to 50–55° C.

The solution of 6.13 kg of amlodipine free base from the preceding step is placed into the reactor A2 and 66 l of ethanol is added. The solution is charged from the reactor A2 through the pressure filter (pressed with nitrogen) to the stirred solution in the reactor A1. The reactor and the filter are washed with 7 l of ethanol. The temperature in A1 increases spontaneously to 65° C. (cooling not necessary). The mixture is then stirred and slowly cooled to 15–20° C. The precipitated solid product is filtered off on a nutche filter, washed on the filter with 2×4 l of ethanol and dried in at temperature of max 40° C.

Yield: 5,85 kg of Amlodipine maleate
Purity (HPLC): <0.05% of aspartate
Particle size-80–100 μm in average
Comparative Process 5 kg of wet amlodipine free base is suspended in 17.5 l of isopropanol. The suspension is heated to 65° C. and a clear solution is obtained. 1.17 kg of maleic acid is added portionwise. Temperature increases to 70° C. and again a clear solution is obtained. Seeding crystals are added and crystallization started, whereby the temperature increases to 72.5° C. The mixture is cooled to 30° C. in 1.5 hours and further cooled to 2° C. in 1 hour. The crystals were filtered off and washed with 3×5.8 l of isopropanol and dried in a vacuum oven at 40° C. for 2 days.

Yield: 4960 g
Purity: 0.63% of Amlodipine aspartate

Example 2

0.58 g of maleic acid is dissolved in 25 ml of water and heated to approximately 60° C. To this solution, 2.0 g of amlodipine is added portionwise. The solution turns slightly yellow during addition and when addition is complete a solid starts to precipitate from the mixture. The mixture is slowly cooled to room temperature and the solid is filtered off. After washing the solid with 5 ml of water, the solid is dried in a vacuum oven at 50° C. for 24 hours leaving 2.4 g (93%) of a white solid.

HPLC: aspartate content 0.01%
NMR: correspond to amlodipine maleate.
Comparative Process:

2 g of amlodipine is suspended in 25 ml of water and heated to approximately 60° C. To this suspension, 0.58 g of maleic acid is added portion wise. The suspension became clear (slightly yellow) and a solid started to precipitate. The mixture was slowly cooled to room temperature and the solid is filtered off. The solid is washed with 5 ml of water and dried in a vacuum oven at 50° C. for 24 hours leaving 2.4 g (93%) of a white solid.

HPLC: aspartate content 0.2%
NMR: amlodipine maleate+approx. 10% of amlodipine free base.

Example 3

Amlodipine Maleate from Amlodipine Hydrochloride 1 g of amlodipine hydrochloride is dissolved in 20 ml of water. To this solution 0.26 g of maleic acid is added and the mixture is stirred until everything is dissolved. After a few minutes a solid precipitates and the mixture is stirred at room temperature for one hour. The solid is filtered off over a paper filter and washed with 2×5 ml of water. After drying in a vacuum oven, 0.72 g (61%) of the product as a solid is obtained.

Aspartate content (HPLC): 0.01%

Example 4

Amlodipine Maleate from Amlodipine Mesylate 1 g of amlodipine mesylate is dissolved in 42 ml of water. 0.23 g of maleic acid is added to this solution and the mixture is stirred until a clear solution is obtained. After a few minutes a solid appears and the mixture is stirred at room temperature for one hour. The solid is filtered off over a paper filter and washed with 2×5 ml of water. After drying in a vacuum oven, 0.73 g (70%) of the product is obtained as an off white solid.

Aspartate content (HPLC): 0.01%

Example 5

Crystallization of Amlodipine Maleate 5 g of amlodipine maleate is dissolved in a mixture of 60 ml of EtOH and 0.055 g of maleic acid at reflux. The solution is cooled in a refrigerator to 5–10° C. and the precipitate is filtered and dried.

Yield: 4.5 g
HPLC (IN): 0.046% of aspartate
Comparative Process 20 g of amlodipine maleate is dissolved in 240 ml of EtOH at reflux. The solution is cooled to 20° C. and the precipitate formed is filtered and dried.

Yield: 16,3 g
HPLC (IN): 0.67% of aspartate

Reference Example

Preparation of the Amlodipine Aspartate as a Reference Standard 16 g of amlodipine and 12 g of amlodipine maleate are melted in a 300 ml flask. The melted substance is cooled to room temperature and dissolved in 300 ml of dichloromethane. The mixture is extracted with 300 ml of a 1M NaOH solution. The organic layer is discarded and the aqueous layer acidified with 55 ml of a 6 M HCl solution. The mixture is extracted with 300 ml of dichloromethane. The layers are separated and the organic layer dried over $Na_2SO_4$. The mixture is evaporated to dryness and the resulting waxy solid recrystallized from ethanol. The obtained sticky solid is dried in a vacuum oven at 40° C. leaving 4.7 g of an off white product.

Yield: 4.7 g (39%)
Mp: 178° C.–183° C.(decomposed)

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

What is claimed is:

1. In a process for making an amlodipine maleate, the improvement which comprises reacting amlodipine or an acid addition salt thereof, other than an amlodipine maleate, with maleic acid under an acidic environment having a pH of 4.5 to 6.5.

2. The process according to claim 1, which comprises:
adding said amlodipine or salt thereof to an equivalent or molar excessive amount of maleic acid.

3. A process for the manufacture of an amlodipine maleate salt substantially free of amlodipine aspartate, which comprises the steps of:
a) adding, continuously or portionwise, a source of amlodipine into a solution or suspension of maleic acid to form a solution, wherein the relative molar amount of maleic acid to amlodipine being added is at least 1.01:1; and
b) separating amlodipine maleate in a solid form from the solution; wherein said amlodipine maleate contains less than 0.2 wt % amlodipine aspartate, based on the amount of amlodipine maleate.

4. The process according to claim 3, wherein the relative molar amount of maleic acid to amlodipine being added is at least about 1.05:1.

5. The process according to claim 3, wherein the source of amlodipine is selected from the group consisting of raw amlodipine obtained after the synthesis of amlodipine; purified amlodipine free base; and an acid addition salt of amlodipine other than the maleate.

6. The process according to claim 5, wherein said source of amlodipine is in a solid state form or dissolved in a solvent.

7. In a process for the manufacture of an amlodipine maleate from amlodipine and maleic acid in solution and separating amlodipine maleate in a solid form from the solution, the improvement which comprises: contacting, continuously or portionwise, a source of amlodipine with a solution or suspension of maleic acid under pH control to form a solution wherein the pH of the solution does not exceed 6.5 and wherein the separated amlodipine maleate contains less than 0.2 wt % amlodipine aspartate, based on the amount of amlodipine maleate.

8. The process according to claim 7, wherein the source of amlodipine is selected from the group consisting of raw amlodipine obtained after the synthesis of amlodipine; purified amlodipine free base; and an acid addition salt of amlodipine other than the maleate.

9. The process according to claim 8, wherein said source of amlodipine is in a solid state form or dissolved in a solvent.

10. The process according to claim 8, wherein said source of amlodipine is an acid addition salt of amlodipine other than the maleate salt, in a solid state or dissolved or suspended in a suitable solvent.

11. The process according to claim 7, wherein said amlodipine source is added to said maleic acid solution or suspension.

12. A process of purification, which comprises:
forming a solution containing amlodipine and maleic acid wherein the molar amount of maleic acid exceeds that of the amlodipine; and
crystallizing or precipitating amlodipine maleate from said solution; wherein said amlodipine maleate contains less than 0.2 wt % amlodipine aspartate, based on the amount of amlodipine maleate.

13. The process according to claim 12, which further comprises converting said amlodipine maleate to another acid addition salt.

14. The process according to claim 13, wherein said amlodipine maleate is converted to amlodipine benzene sulfonate acid or amlodipine hydrochloride.

15. The process according to claim 14, wherein said conversion comprises treating said amlodipine maleate with base to form amlodipine free base and treating said amlodipine free base with benzene sulfonic acid or hydrochloric acid.

16. The process according to claim 12, wherein forming said solution comprises dissolving amlodipine maleate into a solvent and previously, simultaneously or subsequently thereto dissolving maleic acid therein to provide said excess of maleic acid.

17. The process according to claim 12, wherein said excess of maleic acid in said solution is 5 molar % or more.

18. The process according to claim 3, wherein the solution formed in step (a) exhibits a temperature greater than 40° C.

19. The process according to claim 18, which further comprises cooling the solution formed in step (a) to cause precipitation of solid amlodipine maleate.

20. The process according to claim 18, wherein the solution formed in step (a) comprises a solvent selected from water, methanol, ethanol, isopropanol, acetone, acetonitrile, ethyl acetate, toluene, or mixtures thereof.

21. The process according to claim 20, said amlodipine maleate contains less than 0.1 wt % amlodipine aspartate, based on the amount of amlodipine maleate.

22. The process according to claim 7, wherein the temperature during said contacting step is greater than 40° C.

23. The process according to claim 22, which further comprises cooling the solution to cause precipitation of the solid amlodipine maleate.

24. The process according to claim 22, wherein the solution comprises a solvent selected from water, methanol, ethanol, isopropanol, acetone, acetonitrile, ethyl acetate, toluene, or mixtures thereof.

* * * * *

UNITED STATES PATENT AND TRADEMARK OFFICE
CERTIFICATE OF CORRECTION

PATENT NO.         : 6,600,047 B2
APPLICATION NO. : 09/938841
DATED                 : July 29, 2003
INVENTOR(S)       : Benneker et al.

It is certified that error appears in the above-identified patent and that said Letters Patent is hereby corrected as shown below:

On the title page item (63),
In the Related U.S. Application Data:

Change "Dec. 29, 200<u>1</u>" to --Dec. 29, 200<u>0</u>--.

At column 1, line 10:

Change "Dec. 29, 200<u>1</u>" to --Dec. 29, 200<u>0</u>--.

Signed and Sealed this

Twenty-second Day of May, 2007

JON W. DUDAS
*Director of the United States Patent and Trademark Office*